(12) United States Patent
Klein

(10) Patent No.: US 7,578,783 B2
(45) Date of Patent: Aug. 25, 2009

(54) SENSORY EXPERIENCE METHOD AND APPARATUS

(76) Inventor: Jurgen Klein, 756 Mokulua Dr, Kailua, HI (US) 96734

( * ) Notice: Subject to any disclaimer, the term of this patent is extended or adjusted under 35 U.S.C. 154(b) by 801 days.

(21) Appl. No.: 11/050,427

(22) Filed: Feb. 4, 2005

(65) Prior Publication Data

US 2006/0178280 A1     Aug. 10, 2006

(51) Int. Cl.
*A61M 21/00* (2006.01)
(52) U.S. Cl. .................................................. 600/27
(58) Field of Classification Search ............. 600/26–28; 601/52, 58, 16, 116, 148, 149, 55; 607/82, 607/88, 91, 83, 85, 86; 5/451, 933, 900, 5/665–666
See application file for complete search history.

(56) References Cited

U.S. PATENT DOCUMENTS

| | | | |
|---|---|---|---|
| 4,114,205 A | 9/1978 | Müller | |
| 4,424,598 A | 1/1984 | Cima | |
| 4,640,266 A | 2/1987 | Levy | |
| 5,318,503 A * | 6/1994 | Lord | 600/27 |
| 5,819,333 A * | 10/1998 | Coleman | 4/538 |
| 6,169,595 B1 * | 1/2001 | Manne | 352/85 |
| 6,702,767 B1 * | 3/2004 | Douglas et al. | 601/15 |
| 6,913,572 B2 * | 7/2005 | Licht et al. | 600/27 |

FOREIGN PATENT DOCUMENTS

| | | |
|---|---|---|
| EP | 0 098 390 A2 | 1/1984 |
| EP | 0 128 641 A2 | 12/1984 |
| EP | 0 986 985 A1 | 3/2000 |
| FR | 2 836 809 A1 | 9/2003 |
| WO | 02/036063 A2 | 5/2002 |

* cited by examiner

*Primary Examiner*—John P Lacyk
(74) *Attorney, Agent, or Firm*—The Nath Law Group; Jerald L. Meyer; Sung-Yeop Chung

(57) ABSTRACT

A method and apparatus for providing a beneficial stimulation for a human participant which has the participant floating in a pool of liquid and having a sequence of fine water droplets with essential oil directed into an atmosphere above the participant with a matching color of light and sound and then being removed from the atmosphere and replaced with a further atmosphere with fine water droplets and a different essential oil and matching color and sound.

19 Claims, 2 Drawing Sheets

SENSORY EXPERIENCE METHOD AND APPARATUS

BACKGROUND OF THE INVENTION

1. Field of the Invention

The present disclosure relates to both an apparatus in the one case and a method in the other for effecting a beneficial sensory experience for a human participant.

The problem to which this invention is directed relates to both a method and apparatus for providing an olfactory and visual stimulation while reducing other stimulation so as to heighten the positive stimulatory effects.

2. Description of Related Art

It is known to provide relaxation by having a participant float within a body of high-density liquid such as a highly salted water bath.

While floating, the body is supported more or less uniformly so that the effect of gravity is distributed more uniformly so that individual muscle tensions to say, support a limb, can be reduced and especially if the liquid is at about body temperature, then stimuli to the floating body requiring compensation causing possible further tensions for heating or cooling of the body is reduced allowing the brain to focus on other inputs.

It is however, difficult to know what further stimulation might be most appropriate for any individual for instance in the form of visual or olfactory stimulation.

BRIEF SUMMARY OF THE INVENTION

My discovery is that it is feasible to provide over a flotation bath an environment, which includes an atmosphere of fine water droplets, which can be used for intersecting and reflecting light, but also act as a carrier both to introduce and then assist in extraction of an essential oil.

One advantage of this is that, whereas essential oils once introduced into an enclosure would be expected to persist, if they are carried within an atmosphere of fine mist which is fine water droplets then the droplets themselves are more able to be directed and will then be appropriate to both carry in, hold in a dispersed state and then be reasonably effectively extracted by being carried with the water droplets.

What this means then is that there can be an exchange over a relatively smaller period of time of an essential oil.

There can be also a relationship between other sensory inputs and essential oils.

Such other in puts can include a colour or colour combination and in another case it can either be an audible sound or combination of sounds or of course such sounds in the form of music.

Accordingly, one aspect of the present disclosure includes a method of stimulation of the senses for a human participant, the method comprising the steps of having the human participant being supported either directly or indirectly by a body of liquid, and, while floating, having at least stimulation provided by an essential oil or oils combination, and as well, a visual stimulation at the same time, which is provided by a source or sources of light providing light which is directed into an atmosphere of fine water droplets, where the essential oil or oils are carried and dispersed within the fine water droplets.

In a further aspect, the present disclosure includes a method of stimulation of the senses for a participant the method including the steps of supporting the participant either directly or indirectly with a body of liquid so as to cause them to float, and whilst they are floating, providing them with both visual and olfactory stimulation, the visual stimulation being provided by a source or sources of light of selected patterns and/or colour or colours being directed into an atmosphere of the fine water droplets above the participant, there being at least one essential oil as an olfactory stimulant carried by the droplets, and then substantially extracting the fine water droplets together with the essential oil, and replacing these with a fresh atmosphere of fine water droplets and a further essential oil.

In preference, the method includes the further step while the human participant remains floating within the body of liquid, that a first essential oil or oil combination is introduced with or during introduction into an enclosure within which the participant exists and at a selected time thereafter, there is extracted from the enclosure at least to a substantive extent the fine water droplets together with such essential oils that have been collected by such fine water droplets, and thereafter at a further selected time, introducing a further atmosphere of fine water droplets and a further essential oil or oils combination during or with at least this further fine droplet atmosphere.

In preference, during at least some of the period during which a first of the fine droplets have been introduced and are left to remain within the enclosure, there is also provided an input of an audible sound.

In preference, the audible sound is in the form of music, which has been selected to be appropriate to be with the essential oil or oils combination at the time.

In preference, there is a source of light which is coloured so that the coloured light is directed to shine within the enclosure at the least while the fine water droplets are suspended in the atmosphere within the enclosure, and the colour or colours of such light are selected to be appropriate to the essential oil or oils combination within the enclosure at the time.

In preference, the pattern of introducing and extracting an atmosphere of fine water droplets and an accompanying essential oil or oils combination is repeated a plurality of times with a period between such different sets of atmosphere to allow for effective extraction and then further introduction of fresh fine water droplets.

In a further aspect, the disclosure may be said to include an apparatus for assisting in providing beneficial stimulation comprising a body of water within an enclosure, means to introduce into the enclosure a first injection of fine water droplets, a means to introduce into the enclosure at least at sometime during the injection of the said first fine water droplets an essential oil or oils combination, and means to extract from the enclosure to at least a substantive extent fine water droplets within the atmosphere of the enclosure, a means then to effect a further introduction of fine water droplets into the atmosphere of the enclosure with a second essential oil or oils combination, after a selected period of time from the said first extraction of fine water droplets from the enclosure.

In a further aspect, the disclosure may be said to include an apparatus for effecting a beneficial sensory input for a human, the apparatus including a body of liquid within which the human can float, a means to effect an input of fine water droplets into an area immediately above the body of liquid, means adapted to withdraw such fine water droplets, means to effect, in aerosol manner, input of a selected essential oil into the area above the body of liquid, means for lighting the area above the body of liquid, including means adapted to provide colour and/or patterns, and means to effect a sound input into the area for a person floating within the body of liquid to hear, characterized in that there are means to effect in synchronized manner the input and withdrawal of fine water droplets in conjunction with the essential oils, and the input of the noise and colours.

In preference, there is provided a sequenced arrangement for introduction and extraction of fine water droplets together with a sequence of introduction of a selected essential oil or oils combination with each further introduction of fine water droplets.

In preference, there are means to introduce the essential oil or oils into the stream of fine water particles as they are introduced into the enclosure so that at least during some of the time of such introduction, the essential oil or oils combination will be intimately mixed with such fine water particles or droplets.

In preference, there are means to effect a source of light which will effect a lighting of the atmosphere within the enclosure and there are means to effect a colouring of such light from its source, which colour is selected for each of the introduced essential oils.

In other words, there will be a matching sequence of essential oil, colours of lighting and as well a matching audio input.

In preference, there are means to effect a heating of the liquid within the body of water and means to maintain this at a selected temperature, which can be at about body temperature.

In preference, the body of liquid is a high salt content and in preference such salt is Epsom salts, which is to an extent that a human body will float with a substantive proportion of the human body above a level of the liquid in the bath.

In preference, a person would use a flotation pillow for their head if desired and also would have closures for the ears such that liquid would not pass into the ear but such closures would be selected to allow for hearing of audible signals and music through these closures.

In preference, there would be a sequence control which would allow for a selected time for introduction of water vapour with appropriate essential oil or oils combination, a period during which the fine water droplets would be allowed then to remain dormant while the colours are shone through the atmosphere of the enclosure and the sound is played, and then there is a period for extraction and reinsertion of a fresh set of fine water droplets together with a different set of essential oil or oils combination and at the same time a change in the audible sounds and also the colours and patterns selected for this particular further essential oil.

In preference there can be a sequence of these over a period which may be typically a one-hour stretch and six full changes through such a period so that each cycle is through a period of ten minutes.

In this respect, before explaining at least one embodiment of the invention in detail, it is to be understood that the invention is not limited in its application to the details of construction and to the arrangements of the components set forth in the following description or illustrated in the drawing. The invention is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings, which are incorporated in and constitute a part of this specification, illustrate certain embodiments of the invention, and together with the description, serve to explain the principles of the invention.

Those skilled in the art will appreciate that the conception upon which this disclosure is based may readily be utilized as a basis for designing other structures, methods, and systems for carrying out the several purposes of the present invention. It is important, therefore, to recognize that the claims should be regarded as including such equivalent constructions insofar as they do not depart from the spirit and scope of the present invention.

BRIEF DESCRIPTION OF THE DRAWINGS

For a better understanding of this disclosure it will now be described with respect to an exemplary embodiment which shall be described herein with the assistance of drawings wherein.

DETAILED DESCRIPTION OF THE INVENTION

Figure 1:
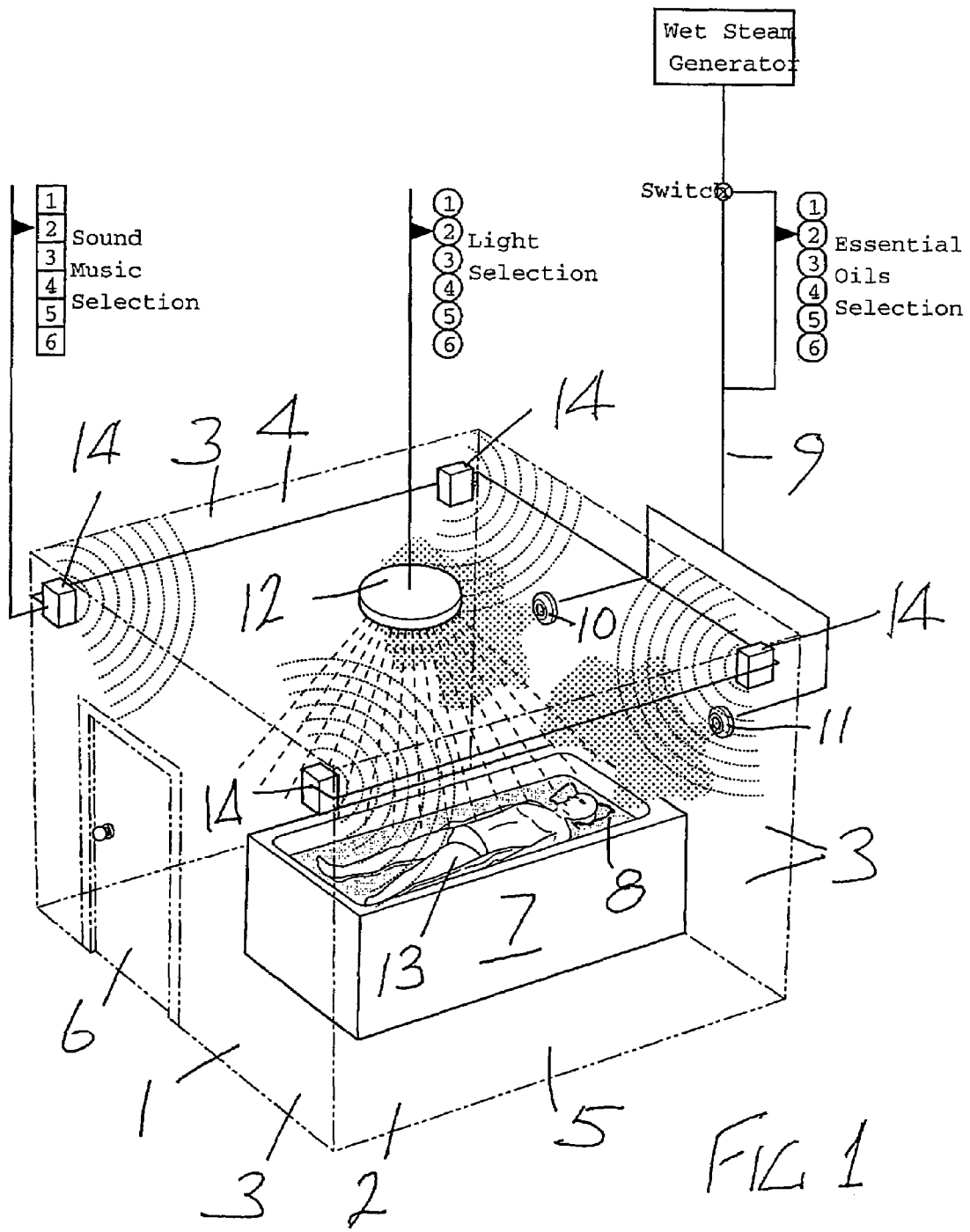
FIG. 1 is a schematic view showing an enclosure with a pool, a person shown typically within the pool, and associated accessories relating to all of these according to the embodiment.

Referring now to FIG. 1, an exemplary embodiment of an apparatus for effecting a beneficial sensory experience for a human participant is illustrated.

Now referring to the drawings and in particular to FIG. 1, there is an arrangement 1 which includes an enclosure 2 which is defined by four walls 3 and a ceiling 4 and of course a floor 5 with access thereto by a door 6.

Within the enclosure thus defined there is a pool 7 which includes liquid 8, which in this case is water with high concentration of Epsom salts to the extent that a participant can float readily within the liquid without assistance and such that a substantive portion of the body is above the level of the liquid.

In our embodiment, additional buoyancy support can be provided for the head of the participant and it has advantage to provide closures against liquid egress into the ear canals, but selected so that sound can still pass generally through such closures. Such devices are commonly available.

There are means to both introduce and extract fine water droplets this being a conduit where the conduit in this case is being shown at 9 and the inlets and outlets being shown at 10 and 11.

There are various ways that fine water droplets can be generated and one of these is to create steam and to allow some of this to condense which then provides a fine mist or fine water droplets which generally then will suspend in conventional atmosphere.

There is also the additional advantage that the fine water droplets maintain a temperature that is at least warm and this then provides an environment that is generally at about a body temperature.

By having fine water droplets in the atmosphere of the enclosure 2, this has two functions, one of which is to carry and distribute essential oils and then secondly, to facilitate the extraction of essential oils after a period of time so that a replacement essential oil without at least substantive contamination of the first essential oil can be achieved.

While reference is made to one essential oil it is possible to use a combination of essential oils at the same time.

However, I have found that there is a beneficial combination of various essential oils and colours of light and in this embodiment then there is provided that there are means to effect a combination of an essential oil selection and a colour of light selection so that these are matched for any particular selected period.

The provision of light is shown in our illustration by a light source 12 and there are means specifically within the light source 12 that control and effect a change in sequence with the selection of essential oils such that there is a matching light for each of the essential oils chosen.

Such devices can be obtained from conventional commercial sources and are typically used in theatrical productions and nightclub environments.

In conjunction with the combination of essential oils and light colour, there is also an additional input namely, music which is also selected to match the colour and essential oil in a particular phase of the stimulaton period.

There can be either music chosen or a tone or tone combination in this embodiment and these are able to be selected prior to the participant being involved in the stimulatory program.

However, in a further embodiment, there are means for the participant to effect a further selection and to interact or change as desired either the length of the stimulation, or a particular combination.

In this particular embodiment there can be means accessible by the participant 13.

There are a plurality of loud speakers at 14, which project sound into the enclosure 2 either in multi-channel form or in mono oral form.

By using a wet steam which produces fine droplets and in this particular case introducing this so that an injected liqiuid, namely a selected essential oil or oils into the wet steam, at least through only a portion of the period of introduction of the steam into the enclosure, a substantive portion of the essential oil will remain with the liquid and by extracting the wet steam from the enclosure 2, there can then be expected to be at least a substantive, if not total, removal of the phase selected essential oil.

One of the difficulties with the arrangement described is that an essential oil when introduced into an enclosure will normally distribute over many of the surfaces and remain generally within the atmosphere of the enclosure over an extended period of time.

By using a wet steam which produces fine droplets and in this particular case introducing this so that an injected liquid, namely a selected essential oil or oils into the wet steam, at least through only a portion of the period of introduction of the steam into the enclosure, a substantive portion of the essential oil will remain with the liquid and by extracting the wet steam from the enclosure 2, there can then be expected to be at least a substantive, if not total, removal of the phase selected essential oil.

Not shown but included within the enclosure is also a fresh air inlet which can also include a means for heating such fresh air to maintain a body temperature of the environment within the enclosure and this can assist then in firstly providing a through flow for steam removal together with the accompanying essential oil.

Figure 2:
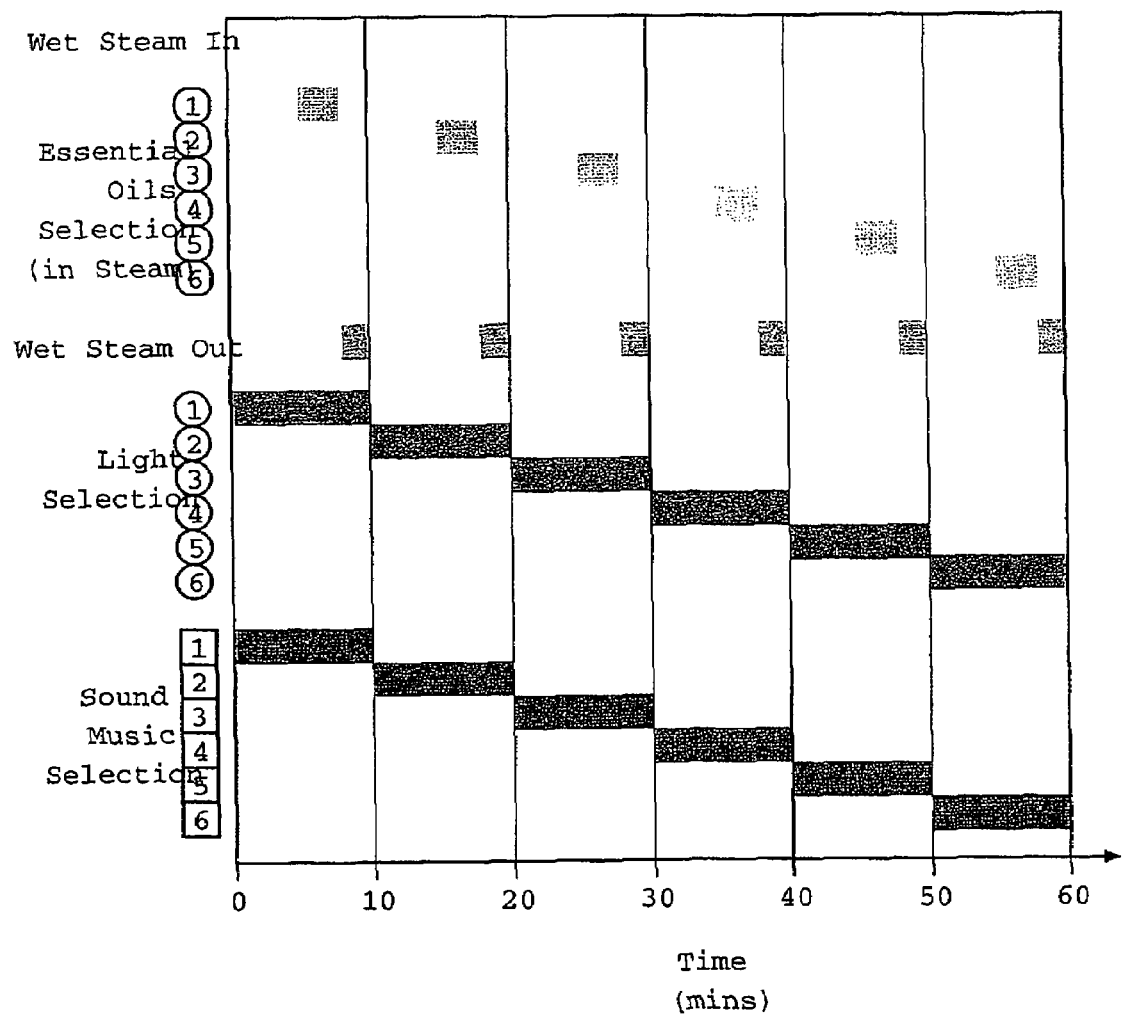
FIG. 2 illustrates a program pattern of introduction of the stimuli according to this embodiment and according to a selected program.

FIG. 2 illustrates in graphical form a program according to the embodiment in which there is provided over a 60 minute period, a sequence of in any ten minute period, a first supply of wet steam in, and during such supply of set steam in, a smaller period during which there is opened a valve into a supply of selected essential oil and by use of suction, a selected proportion of essential oil is thereby pulled into and mixed up with and dissolved by the liquid within the wet steam.

At the same time through the selected phase, there is a coloured light. which is arbitrarily shown as selection 1, and there is a sound choice also as selection 1.

Each of the subsequent phases match the same pattern where there is a selection of essential oils, a colour or as preferred a light pattern with colour and a selected music or sound.

The results in trials conducted so far have shown this method and apparatus to be very effective indeed and able to provide an improved experience for beneficial effect to a human.

Although the invention has been herein shown and described in what is conceived to be the most practical and preferred embodiment, it is recognized that departures can be made within the scope of the invention, which is not to be limited to the details described herein but is to be accorded the full scope of the appended claims so as to embrace any and all equivalent devices and apparatus.

The invention claimed is:

1. A method of stimulation of the senses for a participant the method including the steps of supporting the participant either directly or indirectly with a body of liquid so as to cause them to float, and whilst they are floating, providing them with both visual and olfactory stimulation, the visual stimulation being provided by a source or sources of light of selected patterns and/or colour or colours being directed into an atmosphere of the fine water droplets above the participant, there being at least one essential oil as an olfactory stimulant carried by the droplets, and then substantially extracting the fine water droplets together with the essential oil, and replacing these with a fresh atmosphere of fine water droplets and a further essential oil.

2. The method of stimulation of the senses for a participant as in claim 1, wherein a diffuse colour effect is achieved by introducing the fine water droplets and light into an area immediately above the participant, the coloured lighting and sound being introduced as matching pairs.

3. The method of stimulation of the senses for a participant as in claim 1, wherein the method includes a programmed sequence, wherein the atmosphere of fine water droplets and a first selected essential oil is bathed with a selected colour of light whilst there is also provided a selected music or sound selected for this purpose.

4. The method as in claim 3, wherein there is included the step of extracting the fine water droplets together with the essential oil and inserting replacement fine water droplets and a further selected essential oil, and this is then triggered together with matching further selected colour bathing of the fine water droplets and an audio signal of either music or selected noise.

5. The method as in claim 4, wherein these steps are repeated for a selected number of times with, for each repetition, a different essential oil.

6. The method as in claim 1, wherein the body of liquid and the area above the same into which the fine water droplets and the essential oil or oils are to be introduced, are both within an enclosure.

7. A method as in claim 6, wherein there is included a further step of providing an input of an audible sound during at least some of the period during which a first of the fine droplets have been introduced and are left to remain within the enclosure.

8. The method as in claim 7, wherein the audible sound is in the form of music which has been selected to be with the essential oil or oils combination at the time.

9. The method as claim 6, wherein there is included a further step of directing a source of coloured light into the enclosure at the least while the fine water droplets are suspended in the atmosphere within the enclosure, and the colour or colours of such light are selected for the essential oil or oils combination within the enclosure at the time.

10. The method as in claim 6, wherein there is included a further step that the pattern of introducing and extracting an atmosphere of fine water droplets and an accompanying essential oil or oils combination is repeated a plurality of times with a period between such different sets of atmosphere to allow for effective extraction and then further introduction of fresh fine water droplets.

11. An apparatus for effecting a beneficial sensory input for a human, the apparatus including a body of liquid within which the human can float, a means to effect an input of fine water droplets into an area immediately above the body of liquid, means adapted to withdraw such fine water droplets, means to effect, in aerosol manner, input of a selected essential oil into the area above the body of liquid, means for lighting the area above the body of liquid, including means adapted to provide colour and/or patterns, and means to effect a sound input into the area for a person floating within the body of liquid to hear, characterised in that there are means to effect in synchronised manner the input and withdrawal of fine water droplets in conjunction with the essential oils, and the input of noise and colours.

12. The apparatus as in claim 11, wherein the body of liquid is a floatation pool located within an enclosure.

13. The apparatus as in claim 12, wherein there is provided means to effect a sequenced introduction and extraction of fine water droplets together with a sequenced introduction of a selected essential oil or oils combination with each further introduction of fine water droplets.

14. The apparatus as in claim 13, wherein there are means to introduce the essential oil or oils into the stream of fine water particles as they are introduced into the enclosure so that at least during some of the time of such introduction, the essential oil or oils combination will be intimately mixed with such fine water particles or droplets.

15. The apparatus as in claim 14, wherein there are means to effect a source of light, which will effect a lighting of the atmosphere within the enclosure and means to effect a colouring of such light from its source, which colour is selected for each of the introduced essential oils.

16. The apparatus as in claim 14, wherein there are means to effect a heating of the liquid within the body of water and means to maintain this at a selected temperature, which is approximately the body temperature of a human body.

17. The apparatus as in claim 14, wherein the body of liquid has a high salt content and such salt is Epsom salts, the salt content being sufficient that a human body floating therein will have a substantive proportion of the body above an upper level of the liquid.

18. The apparatus as claim 14, wherein there is a sequence controller which is adapted to effect during a selected time introduction of fine water droplets with an essential oil or oils combination, then a period during which the fine water droplets be allowed then to remain dormant within the enclosure while the colours are shone through the atmosphere of the enclosure and the sound is played, and then there is a-period for extraction and reinsertion of a fresh set of fine water droplets together with a different set of essential oil or oils combination and at the same time a change in the audible sounds and also the colours and patterns selected for this particular further essential oil.

19. An apparatus for assisting in providing beneficial stimulation comprising a body of water within an enclosure, means to introduce into the enclosure a first injection of fine water droplets, a means to introduce into the enclosure at least at sometime during the injection of the said first fine water droplets an essential oil or oils combination, and means to extract from the enclosure to at least a substantive extent fine water droplets within the atmosphere of the enclosure, means then to effect a further introduction of fine water droplets into the atmosphere of the enclosure with a second essential oil or oils combination, after a selected period of time from the said first extraction of fine water droplets from the enclosure.

* * * * *